(12) United States Patent
Lerman et al.

(10) Patent No.: US 7,957,908 B2
(45) Date of Patent: Jun. 7, 2011

(54) SYSTEM, METHOD AND SOFTWARE ARRANGEMENT UTILIZING A MULTI-STRIP PROCEDURE THAT CAN BE APPLIED TO GENE CHARACTERIZATION USING DNA-ARRAY DATA

(75) Inventors: Gilad Lerman, Minneapolis, MN (US); Joseph McQuown, New York, NY (US); Bud Mishra, Great Neck, NY (US)

(73) Assignee: New York University, New York, NY (US)

(*) Notice: Subject to any disclaimer, the term of this patent is extended or adjusted under 35 U.S.C. 154(b) by 1201 days.

(21) Appl. No.: 10/579,811

(22) PCT Filed: Nov. 16, 2004

(86) PCT No.: PCT/US2004/038413
§ 371 (c)(1),
(2), (4) Date: May 16, 2006

(87) PCT Pub. No.: WO2005/050391
PCT Pub. Date: Jun. 2, 2005

(65) Prior Publication Data
US 2007/0100556 A1    May 3, 2007

Related U.S. Application Data

(60) Provisional application No. 60/520,819, filed on Nov. 17, 2003.

(51) Int. Cl.
*G01N 33/48* (2006.01)
*G01N 31/00* (2006.01)
*G06Q 10/00* (2006.01)

(52) U.S. Cl. ............... 702/19; 702/22; 705/1.1

(58) Field of Classification Search .................. None
See application file for complete search history.

(56) References Cited

U.S. PATENT DOCUMENTS 6,221,592 B1 * 4/2001 Schwartz et al. ............... 435/6
6,516,276 B1    2/2003 Ghandour et al.
6,763,308 B2    7/2004 Chu et al.

FOREIGN PATENT DOCUMENTS

WO    WO 99/49403    *    9/1999

OTHER PUBLICATIONS

Pearson K. On lines and planes of closest fir to systems of points in space. Philosophical Magazine. 1901, vol. 2, pp. 559-572.*

(Continued)

*Primary Examiner* — Russell S Negin
(74) *Attorney, Agent, or Firm* — Dorsey & Whitney LLP

(57) ABSTRACT

A system, method and software arrangement are provided that use a fast adaptive multiscale procedure to characterize a random set of points spanning a high dimensional Euclidean space, and concentrated around special lower dimensional subsets. The procedure can be adapted to analyze gene expression data from microarray experiments, and may be applied generally to existing datasets without regard to whether a particular model exists to otherwise describe the dataset. The procedure accordingly can be used for identifying and mathematically isolating stable sets of data points in a given dataset from those in the same dataset that deviate from a stable model under various conditions.

32 Claims, 5 Drawing Sheets

OTHER PUBLICATIONS

Beroza et al. Journal of Computational Chemistry, vol. 17, 1996, pp. 1229-1244.*

Quackenbush J. Microarray data normalization and transformation. Nature Genetics Supplement. Nov. 28, 2002, vol. 32, pp. 496-501.*

Date Validation for the Public Availability of the above Quackenbush article. Retrieved from PUBMED on Nov. 28, 2009, 1 page.*

Delenstarr et al. Estimation of the confidence limits of oligonucleotide array-based measurements of differential expression. Proceedings of the SPIE, vol. 4266, 2001, pp. 120-131.*

Z-score (2004). The Concise Consini Encyclopedia of Psychology and Behavioral Science, 2004. Retrieved online on Sep. 2, 2010 from <<http://www.credoreference.com/entry/wileypsych/z_score>>.*

Mutch et al. "The Limit Fold Change Model: A Practical Approach for Selecting Differentially Expresses Genes from Microarray Data" BMC Bioinformatics 2002, vol. 3, No. 17, pp. 1-11, see entire article, especially col. 1-2, p. 2 and col. 2, p. 3.

Farley et al., "Model-Based Clustering, Discriminant Analysis, and Density Estimation Technical Report No. 380", Department of Statistics, University of Washington, Oct. 2000, see entire article.

He Yang et al. "A segmental nearest neighbor normalization and gene identification method gives superior results for DNA-array analysis", PNAS, Feb. 4, 2003 vol. 100 No. 3 pp. 1122-1127.

B. M. Bolstad, et al. "A comparison of normalization methods for high density oligonucleotide array data based on variance and bias", Bioinformatics 19(2), 2003, pp. 185-193.

Bradley Efron et al. "Empirical Bayes Analysis of a Microarray Experiment", Journal of the American Statistical Association, Dec. 2001, vol. 96, No. 456, pp. 1151-1160.

Peter W. Jones et al. "Rectifiable sets and the Traveling Salesman Problem", Inventiones Mathematicae 102, 1-15, 1990, pp. 1-15.

Michael Parisi et al., "Paucity of Genes on the *Drosophila* X Chromosome Showing Male-Biased Expression", Science, Jan. 31, 2003, vol. 299, pp. 697-700.

Cheng Li et al., "Model-based analysis of oligonucleotide arrays: Expression index computation and outlier detection", PNAS, Jan. 2, 2001, vol. 98, No. 1, pp. 31-36.

Sandrine Dudoit et al., "Statistical methods for identifying differentially expresses genes in replicated cDNA microarray Experiments", Statistica Sinica 12, 2002, pp. 111-139.

Hans-George Muller et al., "Variable bandwidth kernel estimators of regression curves", The Annals of Statistics, vol. 15, No. 1, Mar. 1987, pp. 182-201.

M.A. Newton et al., "On differential variability of expression ratios: improving statistical inference about gene expression changes from microarray data", Journal of Computational Biology, vol. 8, No. 1, 2001, pp. 37-52.

Gilad Lerman, "Quantifying Curvelike Structures of Measures by Using $L_2$ Jones Quantities", Communications on Pure and Applied Mathematics, 2003, pp. 1294-1365.

* cited by examiner

SYSTEM, METHOD AND SOFTWARE ARRANGEMENT UTILIZING A MULTI-STRIP PROCEDURE THAT CAN BE APPLIED TO GENE CHARACTERIZATION USING DNA-ARRAY DATA

CROSS REFERENCE TO RELATED APPLICATIONS

This application claims priority to U.S. provisional patent application No. 60/520,819 filed Nov. 17, 2003.

FIELD OF THE INVENTION

The present invention relates to a system, method and software arrangement for characterizing a random set of points spanning a high dimensional Euclidean space, but concentrated around special lower dimensional subsets that is useful for an analysis of gene expression patterns, gene identifications and characterizations. The system, method and software arrangement can also be employed to extract information from a wide variety of datasets.

BACKGROUND INFORMATION

Microarray and gene-chip technologies provide an approach for characterizing transcriptional properties of thousands of genes and studying their interactions simultaneously under many different experimental conditions. However, in many applications the key problem has been statistical noise in the transcriptional data, varying from experiment to experiment and attributable to non-specific hybridization, cross-hybridization, competition, diffusion of the target on the surface, base-specific structural variations of the probe, etc. A better understanding of this noise can come from the kinetic analysis of the base-pairing, denaturing, and diffusion processes. However, in the absence of detailed knowledge to deconvolve the measurement data, it is hard to distinguish properly between specific clusters of genes, based on expression intensities data. The purpose of identification (combined with normalization) methods is to compare expression intensities from multiple experiments, and distinguish between a stable subset of genes whose behaviors could be expected to be already well-modeled (so-called housekeeping genes, rank-invariant genes, or genes with constant expression), and a subset of genes deviating from the stable model (so-called non-housekeeping genes, regulated genes or differentially expressed genes). See Yang et al., 2002, *Proc. Natl. Acad. Sci. USA* 100(3):1122-1127.

The identification process creates a statistical model of the "main bulk" of the genes (i.e., the stable subset) either through a global statistical analysis of transcriptional expression intensities of all the data, or through a local statistical analysis of similar statistics as a function of the expression range. The genes deviating from the statistics computed via initial identification are then subjected to further analysis to determine their biological characteristics in response to the experimental condition. See e.g. Bolstad et al., 2003, *Bioinformatics* 19(2):185-93.

There is a need for methods and systems that can identify differentially expressed genes from expression data in a data set, particularly from a data set containing data regarding genes expressed under different conditions. Such methods may also be useful for identifying outlying points in any type of statistical data set, where the identified outlying point may represent a meaningful distinction rather than statistical noise.

SUMMARY OF THE INVENTION

In one aspect, methods, software arrangements and systems according to an exemplary embodiment of the present invention are provided that may be used for the analysis of gene expression in a data set to identify statistically meaningful outlying points. In the simplest conceivable setting, it is possible to consider thousands of genes monitored under two different experimental conditions ($c_1$ and $c_2$), and the data in a 2-D Euclidean space thought to consist of average over expression intensities for a gene (g) versus a measure of its relative expression intensities. Such measure of the relative expression intensities may take the form of an expression ratio ("ER"), a logarithm of expression ratio ("LER"), a differential expression ratio ("DE"), etc. For example, if the intensity values $e_{c_1,g}$ and $e_{c_2,g}$, then such values may be described by an expression $$\left(\frac{\ln e_{c_1,g} + \ln e_{c_2,g}}{2}, \ln\frac{e_{c_2,g}}{e_{c_1,g}}\right) \in R^2.$$

According to this exemplary approach it is possible to assume that for a large stable subset of genes any one of these measures of relative expression intensities varies randomly about a mean value from experiment to experiment in a manner which may depend on the different mean values. For instance, the LER may be modeled to have a normal distribution with a variance depending on the local average intensities:

$$\ln\frac{e_{c_2,g}}{e_{c_1,g}} \sim N(0, \sigma(e_g)^2), \tag{1}$$

where $e_g$ is estimated by $(\ln e_{c_1,g} + \ln e_{c_2,g})/2$. In this manner, the area defined by $|y| \leq 3\sigma(\chi)$ may describe a strip containing 99.73% of the housekeeping genes.

In general, the genes belonging to a stable set (e.g. housekeeping genes) may be separated, e.g., by a compact region, from the other genes that respond unambiguously to the change in experimental conditions. The boundary of this region is referred to herein as the "strip," and devising a procedure to compute the strip efficiently and accurately is preferably a mathematical problem addressed by the exemplary embodiments described.

In a broader aspect of the present invention, the methods systems and software arrangements are provided which address the following mathematical problem: Given a set of points in $R^D$ concentrated around a line, a strip may be obtained around the principal axis of the set, so that the strip can isolate deviating points from the main bulk of points. For this problem, a fast multiscale procedure may be provided, and the quality of the computed strip may be estimated.

This exemplary mathematical problem may easily be extended to a procedure to find the strip around a best $L^2$ d-plane, where $1 \leq d < D$. A more general version of this procedure can be used and it can fit a d-dimensional substructure and a strip around it. The later generalization can be used, when d=1, in order to both normalize the genes' expression intensities and identify differentially expressed genes. The methods using the procedure described herein may be used for such identification, assuming the data is normalized around the principal axis. See e.g. Yang et al., 2002, *Proc. Natl. Acad. Sci. USA* 100(3):1122-1127.

The exemplary methods, software arrangements and systems herein use a procedure that may construct three different strips in a multiscale fashion. For the first strip A, it is ascertained at different scales the procedure controls both the number of points outside it, and also the rate of change of such strip in the direction of the principal axis (e.g., a measure of the strip's complexity). The second strip R can maintains at different scales and locations approximately the same ratio between the number of points outside the strip and the total number of points. The third strip S can adaptively estimate the standard deviation of the points more precisely, the strip may estimate adaptively the second moments of the distances of the points from the principal axis. This exemplary multiscale approach is capable of balancing between overfitting at small scales and underfitting at large scales. Exemplary methods, software arrangements and systems that use the procedures describe herein may be used to identify and mathematically isolate stable sets of data points in a given dataset from those in the same dataset that deviate from a stable model under various conditions.

In one exemplary embodiment of the present invention, the software arrangement can include a) a first set of instructions operable to receive at least one dataset, and b) a second set of instructions operable to identify the statistically-outlying data points present in the at least one dataset based on the information contained in the at least one dataset. In exemplary embodiments of the present invention for analyzing genetic data, the dataset typically may comprise data associated with levels of gene expression obtained under two different conditions. In certain exemplary embodiments of the present invention, the two different conditions can reflect the occurrence of at least one of a physiological process, pathophysiological process, oncogenic process, mutational process, pharmacologically-induced process, an immuno-precipitation-induced process, and/or developmental process. For example, the dataset may include a set of N points in $R^D$.

According to further exemplary embodiments of the present invention, the software arrangement can also include one or more of the following additional instructions: c) a third set of instructions operable to store the at least one dataset in a matrix, d) a fourth set of instructions operable to shift each row of the matrix by a center of mass of the at least one dataset, e) a fifth set of instructions operable to compute a principal axis of the at least one dataset, f) a sixth set of instructions operable to rotate the at least one dataset so that the principal axis coincides with x-axis, and/or g) a seventh set of instructions operable to generate strip functions that define boundaries outside which the statistically-outlying data points in the at least one dataset are located. In other exemplary embodiments of the present invention, the strip functions that identify the statistically-outlying data points present in the dataset may be generated by computing the stopping point $F_Q$ using a top-down procedure. The strip functions can be smoothed by the averaging of the strips generated from more than one determination. In addition or alternatively the computation for the stopping point $F_O$ may be set at $Q' \in D(Q_0)$) if: $F_Q > \alpha_0$ or if $|\tilde{Q}| < n_0$ or if $\beta_Q > \delta_0$ or if $|\hat{Q} \backslash \tilde{Q}| > \alpha_1 \cdot |\tilde{Q}'|$. or if $|\hat{Q} \backslash \tilde{Q}| > \alpha_1 \cdot |\tilde{Q}'|$. The stopping point in the computation of $F_Q$ can be applied twice.

BRIEF DESCRIPTION OF TEE DRAWINGS

DETAILED DESCRIPTION

Figure 1:
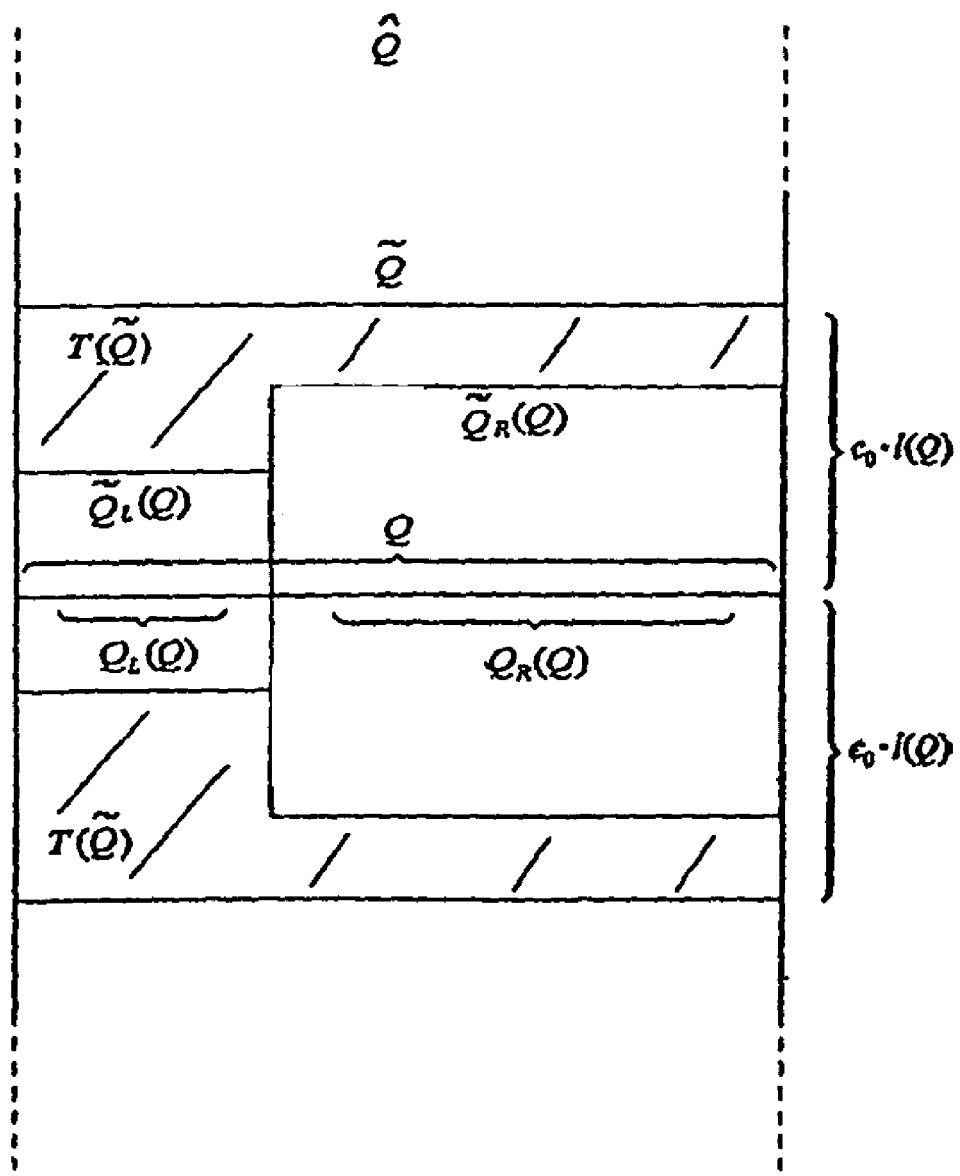
FIG. 1 is an illustration of different parts assigned to the interval Q used by an exemplary embodiment of the method, software arrangement and system according to the present invention.
Figure 2:
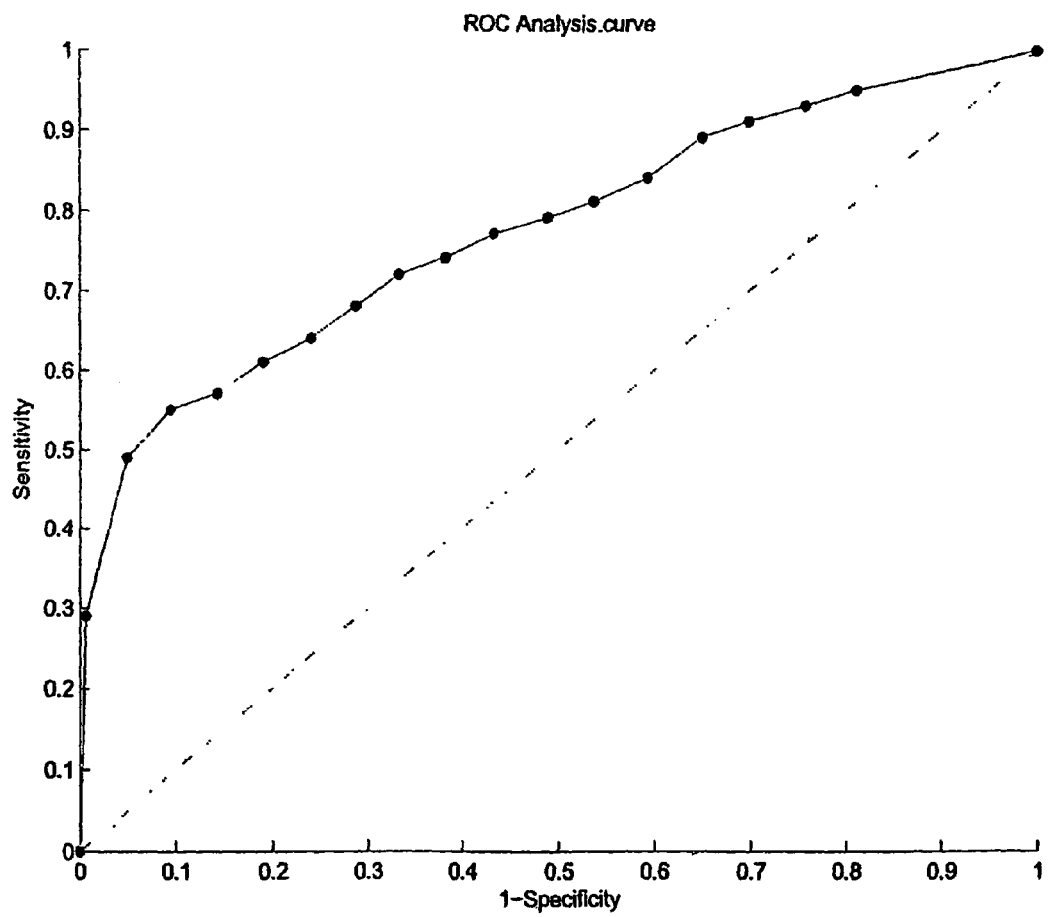
FIG. 2 is an exemplary ROC curve for separating the differentially expressed genes in the synthetic data by the strip $C_O \cdot S$ according to the present invention the dots corresponding to different values of $\alpha_2$.

Description of System, Method and Software Arrangement Employing an Exemplary Procedure I. Input, Preprocessing and Output According to an exemplary embodiment of the present invention, the main input to the procedure is a set $E = \{\chi_i\}_{i=1}^N$ of N points in $R^D$, where $N \geq D$. Additional input may include the following predefined parameters:

$l_0$(integer), $n_0$(integer), $\alpha_i$, i=0, 1, 2(reals), $\delta_0$(real), $c_0$(real) and $C_1$(real, $C_1 > 1$). The parameters $\alpha_i$, i=0, 1, 2, can be established by a user according to an expected ratio of differentially expressed genes over a total number of genes.

The procedure may initially store the set E in an N×D data matrix A, whose rows correspond to the D-dimensional vectors in E. This procedure then may perform (i) the following operations (the notation E and A is maintained for the transformed set and matrix): each row of A is shifted by a center of mass of the set, (ii) "the principal axis", $L \equiv L_E$, of the data set is computed with the principal axis of E being a line spanned by a top right singular vector of a shifted matrix A), and (iii) the set is rotated so that its principal axis coincides with the x axis. Then, an interval $Q_0 = [a_0, b_0]$ of nearly minimal length containing the projection of E is fixed onto L.

The output of the procedure can include three different strip functions, e.g., A, R and S. These are real-valued functions defined on $Q_0$. The procedure may evaluate the strip functions for all points in $P_L E$, where $P_L$ denotes the projection operator from $R^D$ onto L. The envelopes of the strips can be obtained by rotating the graphs of the corresponding functions around the x-axis (the line L).

II. Basic Notation and Definitions

The following notation and definitions may be employed in describing the main part of the exemplary procedure.

$P_L$ denotes the projection operator from $R^D$ onto L (e.g., the principal axis of E).

If K is a subset of $R^D$, $|K| \equiv |K \cap E|$ can denote the number of points of E in K. If Q is an interval, l(Q) may denote its length. $\chi_Q$ denotes the indicator function of Q:

$$\chi_Q(x) = \begin{cases} 1, & \text{if } x \in Q; \\ 0, & \text{otherwise.} \end{cases}$$

The procedure may operate on generalized dyadic grids, which can depend on a fixed rule R for partitioning an interval [a, b) into two subintervals: [a,m) and [m,b) where m=R([a, b)). Either the median rule: $R(Q) = P_L$ (median of $\tilde{Q}$) (as discussed below for the definition of $\tilde{Q}$) or the symmetric rule (equivalently midpoint rule), e.g., $$R([a, b)) = \frac{a+b}{2},$$

may be utilized. The generalized grids $D_j(Q_0) = D_j^R(Q_0)$ may be formed as follows. If $j=0$, then $D_0(Q_0)=\{Q_0\}$. If $j>0$, $Q=[a, b)$ is an interval in $D_j(Q_0)$ and $m=R([a,b))$, then set $$Q_L(Q) := [a, m) \text{ and } Q_R(Q) := [m, b).$$

Define $$D_{j+1}(Q_0) = \bigcup_{Q \in D_j(Q_0)} (Q_L(Q) \cup Q_R(Q)),$$

and $$D(Q_0) = \bigcup_{j=0}^{\ell_0} D_j(Q).$$

If $Q$ is an interval in $D(Q_0)$, its extensions $\hat{Q}$ and $\tilde{Q}$ to $R^D$ may be defined by the formula:

$$\hat{Q} = \{\chi \in R^D : P_L\chi \in Q\},$$

and $$\tilde{Q} = \begin{cases} \{\chi \in \hat{Q} : dist(\chi, L) \leq c_0 \cdot \ell(Q)\} & \text{if } Q \subseteq Q_0; \\ \hat{Q}_0, & \text{if } Q = Q_0. \end{cases}$$

The "top" part of $\tilde{Q}$ can be defined as follows:

$$T(\tilde{Q}) = \tilde{Q} \setminus (\tilde{Q}_L \cup \tilde{Q}_R).$$

If $R$ is any set contained in $\hat{Q}$, then it is possible to define $$\sigma_R = \left(\frac{1}{|R|}\sum_{\chi_1 \in R} dist^2(\chi_1, L)\right)^{\frac{1}{2}} \text{ and } \beta_R = \frac{\sigma_R}{\ell(Q)}.$$

If $Q \in D(Q_0) \setminus \{Q_0\}$, then by $P_Q$ the dyadic parent of $Q$ can be denoted by $P_Q$ according to the grid $D(Q_0)$, and also $P_{Q_0} := Q_0$. may be defined.

FIG. 1 illustrates different parts assigned to the interval Q according to the exemplary embodiment of the present invention.

The Stopping Time Construction

The description of the exemplary procedure can be completed by assigning its stopping time criteria. For each $Q \in D(Q_0)$, it is possible to define $$f_Q = \frac{|T(\tilde{Q})|}{\hat{Q}} \text{ and } F_Q = \sum_{\substack{Q' \in D(Q_0) \\ Q' \supseteq Q}} f_{Q'}.$$

The procedure may compute $F_Q$ with a top-down procedure: First, it initializes $F_Q = 0$ for all $Q \in D(Q_0)$ Then, this exemplary procedure can apply the reduction formula (from coarse levels to fine levels):

$$F_Q = F_{P_Q} + f_Q$$

While proceeding from top to bottom levels, the procedure may stop at an $Q' \in D(Q_0)$ (together with all of its descendants in $D(Q_0)$) if, e.g., one of the following conditions is satisfied:

1. $F_{Q'} > \alpha_0$. (2)

2. $|\tilde{Q}| < n_0$.

3. $\beta_Q > \delta_0$ (optional).

4. $|\hat{Q} \setminus \tilde{Q}| > \alpha_1 \cdot |\tilde{Q}'|$ (optional). (3)

The first stopping time condition can control the number of points outside the different strips (mainly A). The second condition provides valid estimates in each interval. The third condition controls the "complexity" of the strip A. The fourth condition can be used to obtain several equations that control the number of points outside the different strips (mainly A and S). The last two stopping conditions may be ignored by setting $\delta_0 = c_0$ and $\alpha_1 = 1$, respectively.

According to this procedure, it is possible to denote $$\Theta = \{Q : Q \text{ is a stopping time interval in } D(Q_0)\}.$$

Q may be partitioned into two different disjoint sets of "good" and "bad" intervals respectively:

$$G = \{Q \in Q : |\tilde{Q}| \geq n_0 \text{ and } \beta_Q \leq \delta_0\}$$

$$B = \Theta \setminus \Gamma.$$

The Strips A, R and S

Piecewise constant versions of the different strip functions are described as follows. They use the stopping time criteria described earlier, but differ in the manner they select the parameters to determine the stopping time intervals.

In order to assign A, the procedure may compute for each interval $Q \in Q$ the following number:

$$\gamma \tilde{Q} = \begin{cases} \min\{C_1 \cdot \sigma \tilde{Q}, c_0 \cdot \ell(Q)\} & \text{if } Q \in G \\ \min\{C_1 \cdot \sigma \tilde{P}_{Q \cap \tilde{Q}} \cdot c_0 \cdot \ell(Q)\}, & \text{otherwise} \end{cases}$$

The values of A can then be set as follows:

$$A(\chi) = \sum_{Q \in Q} \gamma \tilde{Q} \cdot \chi Q(\chi), \text{ forall } \chi \in P_L E.$$

The strip R may be computed, so that at each stopping time interval Q, this strip R may leave a fraction of size $\alpha^2$ of the points outside the strip. For example, if $Q \in Q$, then $$|\chi : \chi \in \tilde{Q} \text{ and } dist(\chi, L) \geq R(P_L\chi)| = [\alpha_2 \cdot |\tilde{Q}|] \approx \alpha_2 \cdot |\tilde{Q}|,$$

where the "floor function" [x] denotes the largest integer smaller or equal to x. The procedure may compute the strip S as follows:

$$S(\chi) = \sum_{Q \in Q} \sigma \tilde{Q} \cdot \chi Q(\chi).$$

This strip may estimate locally (and e.g., adaptively) the square root of the second moments of the distances of the points of E to the line L.

By multiplying S by a certain constant, an approximate version of $R^T$ may be obtained which is less sensitive to noise.

More precisely, $|\text{set } C_o \equiv C_o(\alpha_1):=\sqrt{2}*\text{erfinv}(\alpha_2),|$ where erfinv is the inverse Erf function (e.g., an error function for normal distribution). If the assumption provided in equation (1) is correct, then the strip $C_o \cdot S$ can leave out a fraction of size $\alpha_2$.

The strips A, R and S constructed as described above may be all piecewise constant functions. It is also possible to derive smooth strip functions as follows: First, generate many instances of the corresponding piecewise constant function according to different grids. Then, average these piecewise constant functions over all the instances.

It is possible to apply the stopping time construction twice or to reiterate the whole algorithm. The resulting strips may be less sensitive to highly deviating points than the original strips.

For gene expression data, it may be preferable to use a smoothed version of the strip $C' \cdot S'$ (e.g., $C'=C_o(\alpha_2)$) without reiteration.

Analysis of the Strips

By an appropriate selection for the stopping time criteria, the number of points outside the strip A may be controlled at different scales as well as the rate of change of A in the direction of the line L. The relation between the strip A and the strips R and $C_o \cdot S$ are also noted.

The set of ancestors of intervals in Q may be denoted by $\Pi$. That is, $P=\{P \in D(Q_0): \exists Q \in Q \text{ such that } P \supseteq Q\}$ $$P=\{P \in D(Q_0): \exists Q \in Q \text{ such that } P \supseteq Q\}$$

For any given interval $Q \in P \backslash Q$ the number of points in $\tilde{Q}$ may be defined outside the strip A as $$m_{\tilde{Q}}(A):=\left|\{x : x \in \tilde{Q} \text{ and } dist(x, L) \geq A(P_L x)\}\right|.$$

Similarly, it is possible to define $$m_{\hat{Q}}(A):=\left|\{x : x \in \tilde{Q} \text{ and } dist(x, L) \geq A(P_L x)\}\right|$$

These numbers may be estimated as follows:
For example, it has been shown that for any $Q \in P \backslash Q$:

$$\frac{m_{\tilde{Q}}(A)}{|\tilde{Q}|} \leq \alpha_0 + \frac{1}{C_1^2} \text{ and } \frac{m_{\hat{Q}}(A)}{\hat{Q}} \leq \alpha_1 + \frac{1}{C_1^2}.$$

Extensively performed numerical experiments can lead to the conclusion that the numbers $m\tilde{Q}(A)$ generally do not depend on the constant $C_1$ (especially for large scale intervals, e.g., $Q_0$). Indeed, it is possible define $$\mu_{\tilde{Q}}(A) := \sum_{Q' \in Q \& Q' \subseteq Q} |\{x : x \in E,$$

$$P_L x \in Q' \text{ and } C_1^\sigma \tilde{Q}' < c_0 \cdot l(Q')c_0 \cdot l(Q') \geq dist(x, L) \geq C_1 \cdot \sigma \tilde{Q}'\}|$$

and the following property may be noted:
If there exists a constant $C'_{\sim} \geq 1$ so that $$\mu_{\tilde{Q}}(A) \leq \left(1 - \frac{1}{C'}\right) \cdot m_{\tilde{Q}}(A), \quad (5)$$

then $$m_{\tilde{Q}}(A) \leq C' \cdot \alpha_0 \cdot |E| \text{ and } m_{\hat{Q}}(A) \leq C' \cdot \alpha_1 \cdot |E|.$$

The exemplary procedure may control, at different scales, the rate of change of the strip A in the direction of the line L, which may be viewed as a complexity of that strip. This property can be formulated as follows:

Assume that for any $$Q \in : \beta_{\hat{P}_Q} \approx \beta_{\hat{P}_Q} \bigcap \hat{Q}$$

and that the grids are symmetric (midpoint rule). If $\Gamma$ is any one of the curves obtained by intersecting the strip obtained by the function A together with a D-plain containing the line L, then $$l(\Gamma \cup Q) \leq (1+C_1 \cdot \delta_0) \cdot l(Q) \text{ for any } Q \in P \backslash Q. \quad (6)$$

The above estimates apply for the strip A. However, the strips $C_1 \cdot S$ and A may be quite similar (e.g., since the values of the functions A and S may depend on the input constant $C_1$). Indeed, the strip A can be obtained by first thresholding the points outside $\cup_{Q \in Q} \tilde{Q}$, and then estimating $C_{1 \cdot \sigma \cdot \tilde{Q}}$ for each $Q \in Q$. Whereas, the strip S estimates $C_{1 \cdot \sigma \cdot \hat{Q}}$ for each $Q \in Q$. The similarity of A and S thus follows from the stopping time condition stated in equation (3), which controls locally the differences between $\tilde{Q}$ and $\hat{Q}$ (there is an additional assumption which is necessary for that similarity; see [9]). The similarity of R and $C_o \cdot S$ has been discussed in the previous section, together with the assumptions under which it holds.

As will be appreciated by one of ordinary skill in the art, the methods of the present invention are typically implemented using a software arrangement and/or a system. The software arrangement can be stored on any suitable medium (e.g., memory, hard drive, CD-Rom, et.) for storing instructions for execution of procedures, and then executed by the systems (e.g., one or more computers). In other embodiments, the instructions in the software arrangement can be transmitted by a suitable carrier signal for execution on a computer processor. The software arrangement may include instructions for applying the procedures described herein for analysis of the data in the data set. In certain embodiments, the software arrangements further include instructions for extracting the data from the data set.

Figure 5:
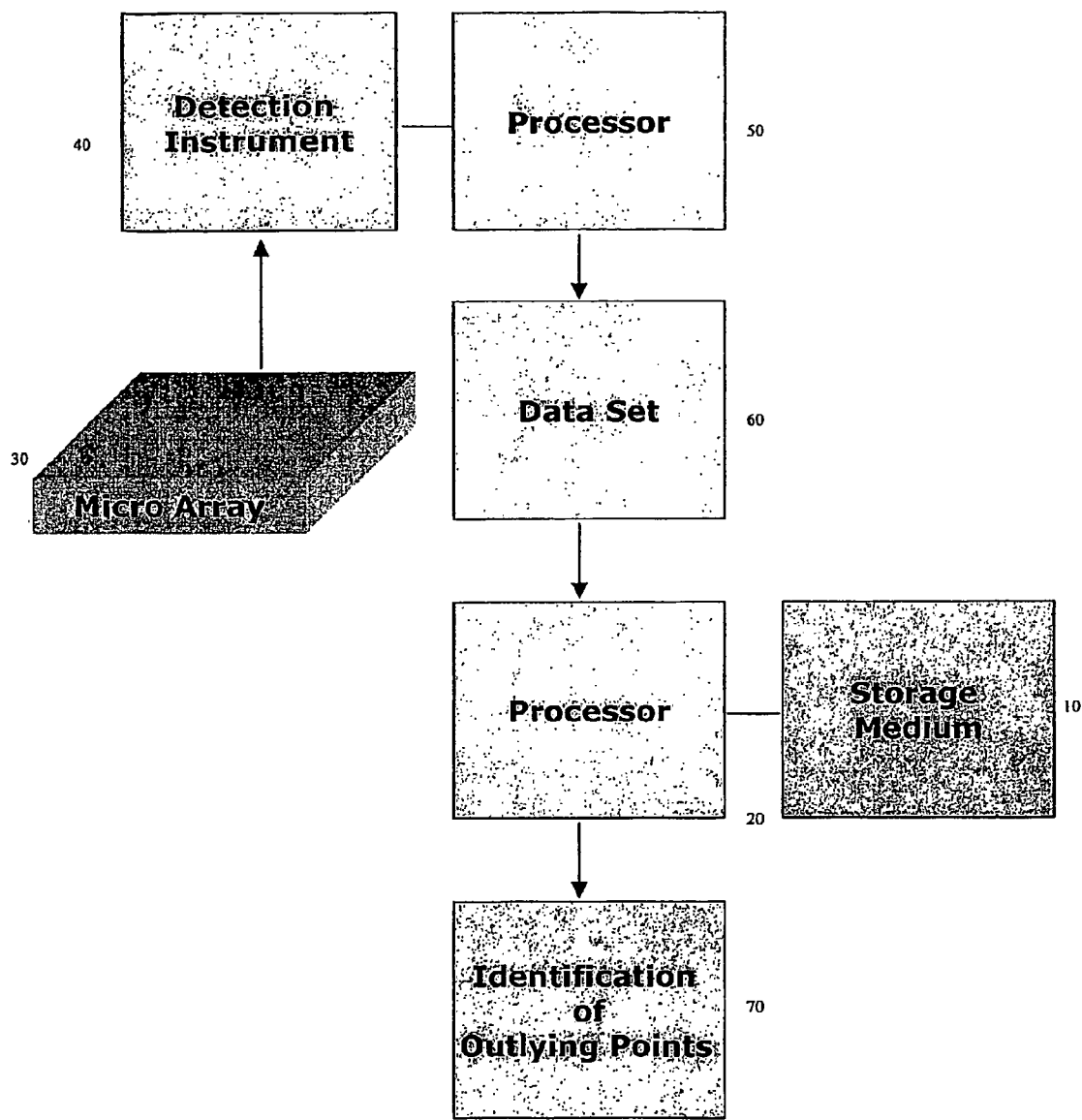
FIG. 5 is a block and flow diagram of the exemplary embodiment of the method and system according to the present invention.

According to an exemplary embodiment of the present invention, the methods and software arrangements described herein are implemented in a system. FIG. 5 illustrates a block diagram of an exemplary embodiment of such a system which also shows a data flow therein. The system includes a storage medium 10, which stores the software arrangement described above for implementing the procedure provided herein. The instructions from the software arrangement may be passed to a processor 20 for executing the instructions. In particular exemplary embodiments, the system may be configured to include original data acquisition components, exemplified by a expression array chip 30 that includes the experimental materials (e.g., hybridization reactions) indicative of gene expression under selected experimental conditions. Gene expression on array chip may be typically indicated by a plurality of different signals (e.g., fluorescence signals) that are detected by a suitable detection system 40. The detected signals from the expression chip 30 can be processed into expression data by a second processor 50, and stored as data set 60. The data in data set 60 may be accessed by the first processor 20 configured with the exemplary software arrangement according to the present invention described herein. The first processor 20 then analyzes the data according to the methods described herein, and may output a result 70 that identifies outlying points indicative of differential gene expression.

Illustration of the Method with Gene Expression Datasets

In the Examples that follow, performance of the multi-strip procedure was examined with a synthetic in silico gene expression data set, generated under a mixture model combining a stable set of genes with a small number of deviating gene expressions. Additionally, the following two applications to genetic data analysis were tested empirically: (i) an experimental is vitro gene expression data set derived from the megaplasmid pSOL1 deficient *C acetobutylicum* strain M5 relative to WT. Yang et al., 2002, *Proc. Natl. Acad. Sci. USA* 100(3):1122-1127; and (ii) a gene expression data set examining the sex-biased genes of *D. melanogaster*. See Parisi et al., 2003, *Science*. 299(5607):697-700.

A. Synthetic Gene Expression Data

For the purpose of testing the procedure according to the present invention two-dimensional synthetic data samples from several types of Gaussian mixture distributions were employed. The synthetic data was used for demonstration and procedure development purposes only. It should be understood that the choice of two dimensions is for illustrative purposes and that the method can be extended to multiple sample gene-chip experiments in higher dimensions.

The data may be simulated as follows. First, an independent identically distributed sample of 5000 points can be created from a mixture of bivariate normal distributions concentrated around the x-axis. This mixture distribution may be denoted by $F_0$. Next, indices of 50 up regulated and 50 down regulated genes can be randomly selected. Further, the distributions of both up and down regulated genes with a similar mixture of Gaussians may be convolved with means in the upper half plane and lower half plane, respectively. The resulting distributions can be denoted by $F_{up}$ and $F_{down}$, respectively.

The class of "stable" genes sampled from the distribution $F_0$ may be denoted by St, the class of up-regulated genes sampled from the distribution $F_{up}$ can be denoted by Up, the class of down-regulated genes sampled from the distribution $F_{down}$ may be denoted by Do and the set of differentially expressed genes (Do∪Up) is denoted by Df. After executing the multiscale procedure, the gene expressions that lie outside the strip $C_o \cdot S$ may be identified as differentially expressed, and referred to as positives (or P). Similarly, the genes inside the strip can be referred to as negatives (or N). The set of true (T) and false (F) positives and negatives are set as follows: TP:=Df∩P, FP:=St∩P, TN:=St∩N and FN:=Df∩N. The sensitivity Sns, the specificity Spc and the error Er may be defined as follows:

$$Sns = \frac{TP}{Df},$$

$$Spc = \frac{TN}{|St|}$$

and $$Er = \frac{1}{2} \cdot \left( \frac{|FP|}{|St|} + \frac{|FN|}{|Df|} \right).$$

Figure 3:
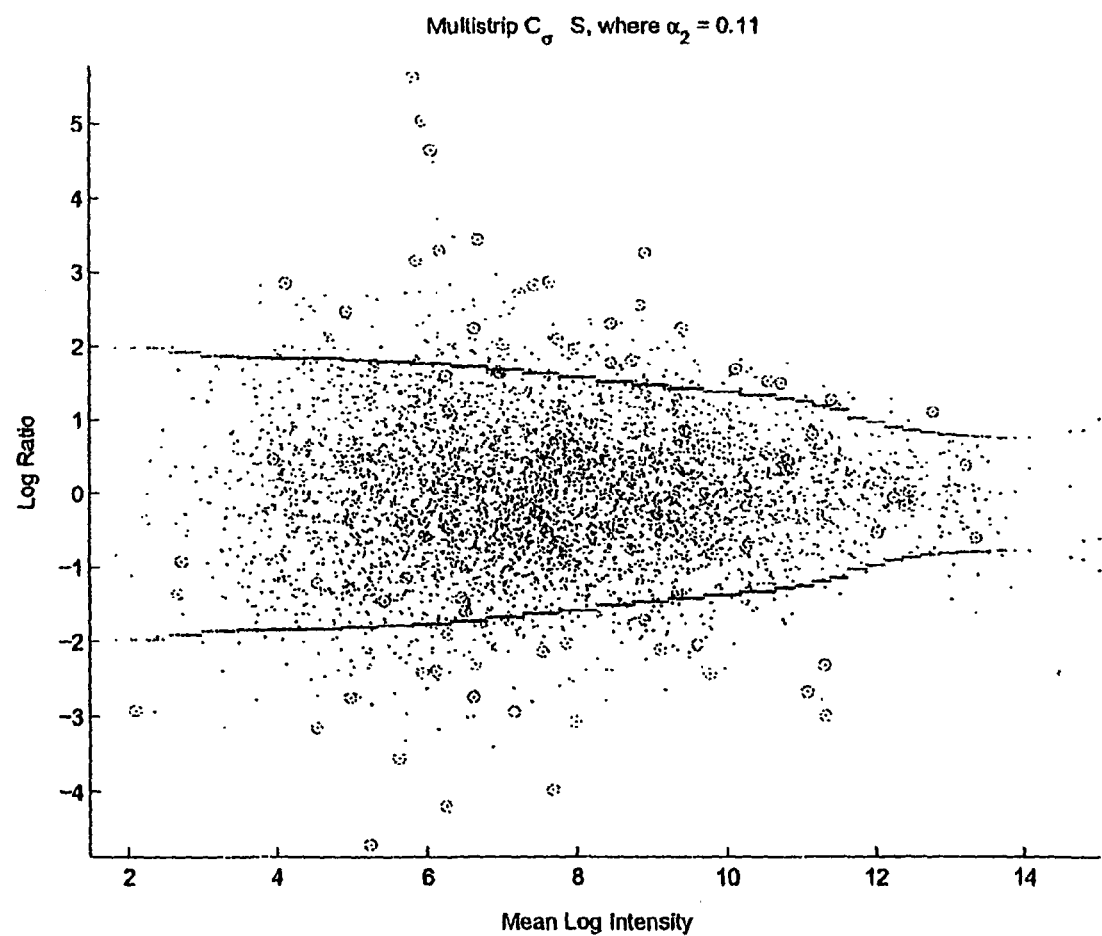
FIG. 3 is an illustration of an exemplary synthetic data set with a multistrip, generated by exemplary embodiments of the present invention with "stable" genes denoted by dots, whereas differentially expressed genes are denoted by circles and the multistrip curve being $C_O \cdot S$, where $\alpha_2 = 0.11$.
Figure 4:
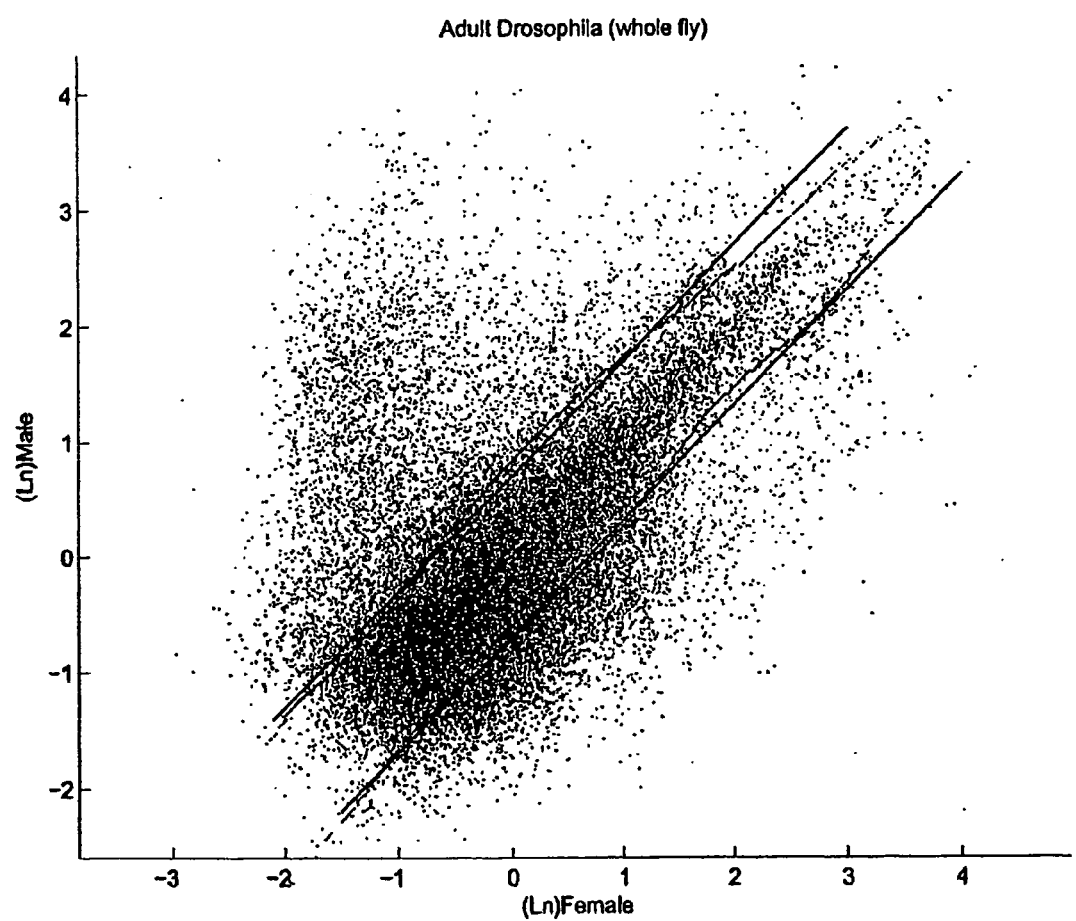
FIG. 4 is an illustration of exemplary logarithmic intensities of *Drosophila melanogaster* whole adult fly, male vs. female, with two lines corresponding to the two-fold strip, two curves corresponding to the nonsymmetric multistrip F.

The ROC curve shown in FIG. 3 is used to demonstrate how well the strip $C_o \cdot S$ separates the differentially expressed genes for different choices of the parameter $\alpha_2$. The area below the piecewise linear ROC curve is 0.78. The error Er is minimized when $\alpha_2$=0.11. FIG. 3 shows an exemplary synthetic data set together with the strip $C_o \cdot S$, where $\alpha_2$=0.11.

Example 1

B. Application of Procedure to *C. acetobutylicum* Gene Expression Data and Comparison with SNNLerm Algorithm The procedure as described herein was tested against a procedure of Yang et al. (*Proc. Natl. Acad. Sci. USA* 2002; 100(3):1122-1127), which was developed using a segmental nearest neighbor method of LERs (SNNLerm) for gene expression normalization and identification. The procedure of Yang et al. divides the log mean intensity range into a fixed number of equidistant intervals and compute the mean and standard deviation of LERs for each interval using only nearest neighbor genes. The value of the strip function ("mask") in each interval is determined by the standard deviation. The procedure of Yang et al. also assigns confidences to the points in each interval.

A comparison of the SNNLerm identification procedure with the procedure described herein was performed using the glass slide arrays of tissue samples taken from the megaplasmid pSOL1 deficient *C. acetobutylicum* strain M5 relative to WT. Yang et al., 2002, *Proc. Natl. Acad. Sci. USA* 100(3): 1122-1127. Strain M5 is isogenic to WT but lacking the pSOL1 plasmid. Only 169 out of the 178 pSOL1 genes are included in the glass slides. The pSOL1 genes are expected to be expressed with a broad range of levels in WT, but unexpressed in M5. Therefore, the expression ratios of these genes should be characterized as non-differentially expressed and even down-regulated. This classification depends on whether such a deviating gene is actually expressed in WT or not. Six glass arrays were used, which were selected by Yang et al., (*Proc. Natl. Acad. Sci. USA* 2002; 100(3):1122-1127) to produce Table 1. See Yang et al., 2002, *Proc. Natl. Acad. Sci. USA* 100(3):1122-1127 at 1126. Each slide was analyzed separately. After pre-filtering and normalizing each slide by the initial part of the SNNLerm procedure, the strip $C_o \cdot S$ was used for the multiscale algorithm. In order to be able to compare between the two procedures, the value of $\alpha_2$ was determined in order to obtain the same average fraction (averaged over the six slides) of pSOL1 genes identified by both procedures as differentially expressed over the total number of those genes.

The error of identification specified in equation 9 of Yang et al. (*Proc. Natl. Acad. Sci. USA* 2002; 100(3):1122-1127) was used. More specifically, the set of pSOL1 genes in each experiment was denoted by Df and the complementary set denoted by St. Gene expressions that lie outside the assigned strip (or with confidences greater than 95.5 when using the SNNLerm algorithm) are identified as differentially expressed and referred to as positives (or P). The notations P, N, TP, FP, TN and FN are used as in the previous section. Also denote by DU the points of the set Df, which the given algorithm identified as up regulated (that is, above the strip). $\tilde{E}r$ is defined as follows:

$$\tilde{Er} = \frac{1}{2} \cdot \left( \frac{|FP|}{|St|} + \frac{|FN| + |DU|}{|Df|} \right).$$

The results are summarized in Table 1. Df less than 169 due to pre-filtering of pSOL1 genes with high background noise. The multiscale procedure performs better than the SNNLerm algorithm for slides numbers: 422, 424, 805, while SNNLerm performs better for slide number: 784. The two procedures are comparable for slides numbers: 783 and 786. Unlike the SNNLerm algorithm, the multiscale procedure is adaptive. In particular, parameter values are independent of the types of microarray experiments (glass, vinyl, plastic).

TABLE 1

Comparison of SNNLerm and the Multistrip method for identification of *C. acetobutylicum* pSOL1 genes in six slides of M5-WT experiments.

| | Numerical Results | | | | | |
|---|---|---|---|---|---|---|
| | Slide 422 | Slide 424 | Slide 783 | Slide 784 | Slide 786 | Slide 805 |
| Table Count | | | | | | |
| \|Df\| | 118 | 127 | 51 | 144 | 119 | 136 |
| \|St\| | 655 | 645 | 551 | 742 | 653 | 706 |
| SNNLerm | | | | | | |
| \|FP\| | 58 | 47 | 38 | 34 | 37 | 41 |
| \|FN\| | 106 | 115 | 47 | 107 | 95 | 111 |
| \|DU\| | 1 | 1 | 1 | 0 | 0 | 1 |
| \|TP\| | 12 | 12 | 4 | 37 | 24 | 25 |
| $\tilde{Er}$ | 0.498 | 0.493 | 0.505 | 0.394 | 0.427 | 0.441 |
| Multiscale | | | | | | |
| \|FP\| | 61 | 43 | 38 | 36 | 32 | 41 |
| \|FN\| | 103 | 112 | 47 | 109 | 96 | 108 |
| \|DU\| | 1 | 1 | 1 | 0 | 0 | 1 |
| \|TP\| | 15 | 15 | 4 | 35 | 23 | 28 |
| $\tilde{Er}$ | 0.487 | 0.478 | 0.505 | 0.403 | 0.428 | 0.430 |

Example 2

C. Application of the Method to *D. melanogaster* Gene Expression Data and Sex-Biased Genes The glass, vinyl, plastic provided herein also was applied to detect sex-biased genes of *Drosophila melanogaster* using one of the many experiments of Parisi et al. (*Science* 2003; 299(5607):697-700). In this experiment, tissue is taken from adult male versus adult female flies without having removed their reproductive organs (slide is available from the Gene Expression Omnibus under accession GSM2456).

Global gene expression in *Drosophila melanogaster* has been reported to have an elevated transcription of X-chromosome genes in males due to a dosage-compensation mechanism. However, unlike in the somatic cells, there is likely no dosage compensation in the germ line and this hypothesis can be tested by comparing expression data in males against expression data in females (of both somatic, germ line and mixed cells).

In order to distinguish between male-biased and female-biased genes and also due to the non-symmetric nature of the data, a slight variation of the multiscale procedure was implemented. That is, the procedure was run twice for the two sets of genes in the two half planes bisected by the diagonal of the data. This line was used instead of the principal axis, thus avoiding the initial transformation of the algorithm.

Parisi et al. (*Science* 2003; 299(5607):697-700) used the threshold ln 2 to determine the differentially expressed genes (two fold approach). In order to compare their constant strip with the one generated by the exemplary procedure described herein, $\alpha_2$ was set for each subset (in each half plane) so that the number of genes outside both strip are the same. For the sake of simplicity, the strip R was used. The resulting strip together with the two fold strip are shown in FIG. 3.

Conclusions

The multiscale procedure used by the system, method and software arrangement according to the present invention described herein is a robust, efficient and mathematically innovative way to adaptively analyze data without prescribing assumptions to the data when little prior information is available. Thus, this and other such priorless approaches depart from conventional statistical methods as well as Bayesian methods in that one is no longer required to access a model, or to fit to a model through optimization of a likelihood, expectation, or related functions (e.g. MCMC, or MLE methods). Even empirical Bayes methods (Efron et al., 2001, *J. Amer. Stat. Assoc.* 96:1151-1160) cannot reconcile the problems of non-specific hybridization, cross-hybridization, competition, target diffusion, probe-specific complications, etc., that happen at the local level. Any algorithm that pre-determines the localities of the expression level also undermines analysis. In any case, through local spatial adaptability, the focus of this multiscale procedure becomes a low-complexity representation of the structure in the data without ascribing parametric distributions. See Jones, 1990, *Invent. Math.* 102(1):1-15; David and Semmes, 1993, *Analysis of and on Uniformly Rectifiable Sets*, Volume 38 of the American Mathematical Society, Providence, R.I.; Lerman, 2003, *Comm. Pure App. Math.* 56(9):1294-1365. Furthermore, the complexity of the representation is provably bounded by a "competitive factor" with respect to the best possible representation. Other algorithmic examples of similar approach include CART (Breiman et al., 1983, *Classification and Regression Trees*, Wadsworth, N.Y.), MARS (Friedmnan, 1992, *Annals of Statistics*, 19:1-67), MART, variable bandwidth kernel methods (Muller and Stadtmuller, 1987, *Annals of Statistics* 15(1):182-201), etc.

The approach to gene expression data described herein may resolve many important difficulties in comparing poorly understood variations in gene-expression measurements from experiment to experiment. Moreover, the exemplary procedure described herein is provided for analyzing gene expression data to other techniques, and for defining and elucidating genes with putative differential expression as well as methods for normalization and experimental control. See Li and Wong, 2001, *Proc. Natl. Acad. Sci. USA* 98(1):31-36; Dudoit et al., 2002, *Statistica Sinica* 12(1):111-139; Efron et al., 2001, *J. Amer. Stat. Assoc.* 96:1151-1160; Garrett and Parmigiani, 2003, *The Analysis of Gene Expression Data*, Chapter 16, Springer-Verlag, New York; Yang et al., (*Proc. Natl. Acad. Sci. USA* 2002; 100(3):1122-1127; and Newton et al., 2001, *J. Computat. Biol.* 8:37-52. Three datasets (e.g., one synthesized and two experimental) were examined, and from these examinations it may be concluded that multi-scale approach in its most skeletal form captures the local variations well, even when it has no direct way of modeling the nature of the variation.

The exemplary procedure utilized by the system, method and software arrangement described herein provides several advantages over previous procedures as it is readily adaptable to different types of arrays of different sizes. Therefore, the procedure is more robust than previous approaches. Second, the exemplary procedure runs in time linear in the number of points examined and hence faster than other approaches. Third, the non-parametric approach of the procedure easily adapts to existing datasets, and does not reinforce artificial assumptions on the distribution of expression intensities. Fourth, the procedure more accurately isolates and identifies variable data points from stable data points in a given dataset, and therefore exhibits a performance superior to other previously disclosed procedures.

While the present disclosure illustrates exemplary embodiments where the methods provided herein are implemented for determination of differential gene expression using a data set of gene expression data, the procedures provided herein are equally applicable to any statistical dataset of information that can be represented in two or more dimensions. The procedure is general enough in nature to be useful in any embodiment where it is desirable to find lower dimensional representations of data in higher dimensions. By way of example, but not limitation, the methods provided herein can be implemented with data sets that contain data concerning financial information, such as trends in stocks, commodities, or currencies under variable condition, where it is desirable to identify unusually deviating items in the data base.

Various publications have been cited herein, the contents of which are hereby incorporated by reference in their entireties.

The invention claimed is:

1. A process for determining statistically-outlying data points present in at least one dataset, comprising:
   a) receiving the at least one dataset;
   b) determining at least one interval associated with the dataset;
   c) using a hardware processing arrangement which comprises a processor, determining a plurality of subintervals of the at least one interval by iteratively dividing at least one of the at least one interval more than once until at least one predetermined criteria is met; and
   d) determining the statistically-outlying data points present in the at least one dataset, wherein each data point is associated with a particular subinterval of the subintervals, and wherein the determination is performed based on information related to the subintervals and as a function of the length of the particular subinterval of the subintervals associated with the particular data point.

2. The process of claim 1, wherein the at least one dataset comprises data associated with levels of gene expression obtained under at least two different conditions.

3. The process of claim 2, wherein the different conditions reflect an occurrence of at least one of a physiological process, a pathophysiological process, an oncogenic process, a mutational process, a pharmacologically-induced process, an immuno-precipitation-induced process, or a developmental process.

4. The method of claim 1, wherein the at least one data set comprises data associated with financial trends.

5. The process of claim 1, further comprising: at least one of displaying or storing the statistically-outlying data points in a storage arrangement in at least one of a user-accessible format or a user-readable format.

6. The process of claim 1, wherein at least one of the at least one predetermined criteria is a function of a portion of the dataset being contained in one of the subintervals.

7. The process of claim 6, wherein the data set comprises a total number of points, and wherein at least one of the at least one criteria is a function of a predetermined ratio of the statistically-outlying points to the total number of points.

8. The process of claim 1, wherein the subintervals are determined based on a dyadic grid division procedure.

9. The process of claim 1, wherein each of the statistically-outlying data points is further determined as a function of a distance of each point to a principal axis of the dataset.

10. The process of claim 1, wherein each particular subinterval of the subintervals comprises a respective region having a height, wherein the height is determined as a function of the length of the subinterval, and wherein each of the statistically-outlying data points is located outside of the respective region of the particular subinterval with which the statistically-outlying data point is associated.

11. The process of claim 10, wherein at least one of the at least one predetermined criteria is based on the number of points located within each region being below a predetermined threshold.

12. The process of claim 10, wherein the at least one dataset comprises a total number of points, wherein each particular subinterval of the subintervals comprises a total number of points, and wherein at least one of the at least one criteria is based on a constraint that a ratio of a number of points located outside each region to the total number of points in the particular subinterval exceeds a ratio of the number of statistically-outlying points in the dataset to the total number of points in the at least one dataset.

13. The process of claim 10, wherein at least one of the at least one predetermined criteria is based on an average distance of the total number of points located in each of the regions to a principal axis of the at least one dataset.

14. A non-transitory storage medium which includes thereon a software arrangement to be executed by a hardware processing arrangement for determining statistically-outlying data points present in at least one dataset, the software arrangement comprising:
   a) a first set of instructions operable to configure the processing arrangement to receive the at least one dataset;
   b) a second set of instructions operable to configure the processing arrangement to determine at least one interval associated with the dataset;
   c) a third set of instructions operable to configure the processing arrangement to determine a plurality of subintervals of the at least one interval by iteratively dividing at least one of the at least one interval more than once until at least one predetermined criteria is met; and
   d) a fourth set of instructions operable to configure the processing arrangement to determine the statistically-outlying data points present in the at least one dataset, wherein each data point is associated with a particular subinterval of the subintervals, and wherein the determination is performed based on information related to the subintervals and as a function of the length of the particular subinterval of the subintervals associated with the particular data point.

15. The storage medium of claim 14, wherein the at least one dataset comprises data associated with levels of gene expression obtained under at least two different conditions.

16. The storage medium of claim 15, wherein the different conditions reflect the occurrence of at least one of a physiological process, a pathophysiological process, an oncogenic process, a mutational process, pharmacologically-induced process, an immuno-precipitation-induced process, or a developmental process.

17. The storage medium of claim 14, wherein the at least one data set comprises data associated with financial trends.

18. The storage medium of claim 14, wherein the software arrangement further comprises: a further set of instructions operable to configure the processing arrangement to at least one of display or store the statistically-outlying data points in a storage arrangement in at least one of a user-accessible format or a user-readable format.

19. The storage medium of claim 14, wherein at least one of the at least one predetermined criteria is a function of a portion of the at least one dataset being contained in one of the subintervals.

20. The storage medium of claim 19, wherein the at least one dataset comprises a total number of points, and wherein at least one of the at least one predetermined criteria is a function of a predetermined ratio of the statistically-outlying points to the total number of points.

21. The storage medium of claim 14, wherein the subintervals are determined based on a dyadic grid division procedure.

22. The storage medium of claim 14, wherein each of the statistically-outlying data points is further determined as a function of a distance of each point to a principal axis of the at least one dataset.

23. The storage medium of claim 14, wherein each particular subinterval of the subintervals comprises a region having a height, wherein the height is determined as a function of the length of the subinterval, and wherein each of the statistically-outlying data points is located outside of the region of the particular subinterval with which the statistically-outlying data point is associated.

24. The storage medium of claim 23, wherein at least one of the at least one predetermined criteria is based on the number of points located within each of the regions being below a predetermined threshold.

25. The storage medium of claim 23, wherein the data set comprises a total number of points, wherein each particular subinterval of the subintervals comprises a total number of points, and wherein at least one of the criteria is based on a constraint that a ratio of the number of points located outside each region to a total number of points in the particular subinterval exceeds a ratio of the number of statistically-outlying points in the at least one dataset to the total number of points in the at least one dataset.

26. The storage medium of claim 23, wherein at least one of the at least one predetermined criteria is based on an average distance of a total number of points located in each of the regions to a principal axis of the at least one dataset.

27. A system for determining statistically-outlying data points present in at least one dataset, comprising:
  a hardware processing arrangement which includes a processor and which is operably configured to:
  a) receive the at least one dataset;
  b) determine at least one interval associated with the dataset;
  c) determine a plurality of subintervals of the at least one interval by iteratively dividing at least one of the at least one interval more than once until at least one predetermined criteria is met; and d) determine the statistically-outlying data points present in the at least one dataset, wherein each data point is associated with a particular subinterval of the subintervals, and wherein the determination is performed based on information related to the subintervals and as a function of the length of the particular subinterval of the subintervals associated with the particular data point.

28. The system of claim 27, further comprising a further hardware processing arrangement configured to generate the at least one dataset, wherein the further hardware processing arrangement comprises a further processor.

29. The system of claim 28, further comprising a detector configured to detect a plurality of signals indicative of gene expression and convert the detected signals into the at least one dataset.

30. The system of claim 27, wherein the processing arrangement is further operably configured to at least one of display or store the statistically-outlying data points in a storage arrangement in at least one of a user-accessible format or a user-readable format.

31. The system of claim 27, wherein the subintervals are determined based on a dyadic grid division procedure, wherein each particular subinterval of the subintervals comprises a region having a height, wherein the height is determined as a function of the length of the particular subinterval, wherein each of the statistically-outlying data points is located outside of the region of the particular subinterval with which the statistically-outlying data point is associated, wherein the at least one dataset comprises a total number of points, wherein each particular subinterval comprises a total number of points, and wherein one or more of the at least one predetermined criteria is based on at least one of (i) a portion of the at least one dataset being contained in one of the subintervals, (ii) a predetermined ratio of the statistically-outlying points to the total number of points, (iii) the number of points located within each of the regions being below a predetermined threshold, (iv) a constraint that a ratio of the number of points located outside each of the regions to the total number of points in the particular subinterval exceeds a ratio of the number of statistically-outlying points in the at least one dataset to the total number of points in the at least one dataset, or (v) an average distance of the total number of points located in each of the regions to a principal axis of the at least one dataset.

32. The system of claim 27, wherein the subintervals are determined based on a dyadic grid division procedure, wherein each particular subinterval of the subinterval comprises a region having a height, wherein the height is determined as a function of the length of the particular subinterval, wherein each of the statistically-outlying data points is located outside of the region of the particular subinterval to which the statistically-outlying data point is associated, wherein the at least one dataset comprises a total number of points, wherein each subinterval comprises a total number of points, and wherein one or more of the at least one predetermined criteria is based on at least two of (i) a portion of the at least one dataset being contained in one of the subintervals, (ii) a predetermined ratio of the statistically-outlying points to the total number of points, (iii) the number of points located within each of the regions being below a predetermined threshold, (iv) a constraint that a ratio of the number of points located outside each of the regions to the total number of points in the particular subinterval exceeds a ratio of the number of statistically-outlying points in the at least one dataset to the total number of points in the at least one dataset, or (v) an average distance of the total number of points located in each region to a principal axis of the at least one dataset.

* * * * *